(12) United States Patent
Graumann et al.

(10) Patent No.: US 7,597,473 B2
(45) Date of Patent: Oct. 6, 2009

(54) X-RAY RECORDING DEVICE WITH AN X-RAY DETECTOR AND AN X-RAY EMITTER

(75) Inventors: Rainer Graumann, Höchstadt (DE); Erwin Lutz, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/680,727

(22) Filed: Mar. 1, 2007

(65) Prior Publication Data

US 2007/0211863 A1  Sep. 13, 2007

(30) Foreign Application Priority Data

Mar. 10, 2006  (DE)  ........................ 10 2006 011 234

(51) Int. Cl.
*H05G 1/02* (2006.01)
(52) U.S. Cl. ........................ 378/197; 378/196; 378/198
(58) Field of Classification Search .......... 378/196–198
See application file for complete search history.

(56) References Cited

U.S. PATENT DOCUMENTS

| | | | | |
|---|---|---|---|---|
| 4,955,046 A * | 9/1990 | Siczek et al. | ................. | 378/197 |
| 4,964,151 A * | 10/1990 | Trotel | ......................... | 378/198 |
| 5,038,371 A * | 8/1991 | Janssen et al. | .............. | 378/197 |
| 5,050,204 A * | 9/1991 | Siczek et al. | ................. | 378/197 |
| 5,067,145 A * | 11/1991 | Siczek et al. | ................. | 378/198 |
| 5,515,416 A * | 5/1996 | Siczek et al. | ................. | 378/197 |
| 5,521,957 A * | 5/1996 | Hansen | ........................ | 378/198 |
| 5,627,873 A | 5/1997 | Hanover et al. | | |
| 5,642,395 A | 6/1997 | Anderton et al. | | |
| 6,139,183 A | 10/2000 | Graumann | | |
| 6,213,638 B1 | 4/2001 | Rattner | | |
| 6,234,672 B1 * | 5/2001 | Tomasetti et al. | ........... | 378/197 |
| 6,264,364 B1 * | 7/2001 | Pflaum et al. | ................ | 378/196 |
| 6,272,368 B1 * | 8/2001 | Alexandrescu | ............... | 600/407 |
| 6,382,833 B2 * | 5/2002 | Leandersson et al. | ....... | 378/197 |
| 6,431,751 B1 * | 8/2002 | Everett et al. | ................ | 378/197 |
| 6,742,929 B2 * | 6/2004 | Horbaschek | ................. | 378/197 |
| 7,018,097 B2 * | 3/2006 | Schmitt | ....................... | 378/197 |
| 2004/0008820 A1 * | 1/2004 | Schmitt | ....................... | 378/193 |

* cited by examiner

*Primary Examiner*—Edward J Glick
*Assistant Examiner*—Thomas R Artman
(74) *Attorney, Agent, or Firm*—Schiff Hardin LLP

(57) ABSTRACT

An X-ray recording device has an X-ray detector and an X-ray emitter aligned with one another on a mobile supporting device, the supporting device being supported by retainer on a stand unit and being displaceable along a horizontal translation axis and/or vertical translation axis. The retainer has only one first pivoting arm rotatably mounted on the stand unit for rotation around a first vertical rotational axis and only one second pivoting arm rotatably mounted on the first pivoting arm for rotation around a second vertical rotational axis. This X-ray recording device allows an alteration to the recording range to be undertaken at reduced cost and with a space-saving and stable configuration.

14 Claims, 2 Drawing Sheets

X-RAY RECORDING DEVICE WITH AN X-RAY DETECTOR AND AN X-RAY EMITTER

BACKGROUND OF THE INVENTION

1. Field of the Invention

The present invention relates to an X-ray recording (imaging) device with an X-ray detector and an X-ray emitter, which are aligned with one another on a mobile supporting device, the supporting device being supported by a retainer on a stand unit and being displaceable along a horizontal translation axis and/or a vertical translation axis.

2. Description of the Prior Art

X-ray devices and/or X-ray recording devices are a substantial aid in medical procedures, in spite of advancing developments and further possibilities in the field of radiation-free medical diagnosis. X-ray recording devices, therefore, are encountered in a large number of medical applications. The applications range from X-ray diagnosis, for example the diagnosis of bone fractures, tumors, cysts, calcification, entrapped air or even medical check-ups, including X-ray examinations, for example in angiograms, monitoring of medical interventions or location of medical instruments, etc. X-ray recording devices of the aforementioned type are frequently C-arm X-ray devices, which are becoming increasingly established due to their advantages in the medical field.

The advantages of C-arm X-ray devices include the possibility of spatial representations of an object and/or a patient while at the same time establishing good accessibility thereto, which is important particularly for medical interventions. Furthermore, there is the possibility of producing C-arm X-ray devices with a mobile design, which increases the applications—for example for use with bed-ridden patients—and reduces costs.

In order to detect a spatial representation, for example of a patient, part of a patient, or an organ, generally the C-arm is rotated around the patient in a motorized manner along its circumference by means of a drive. During the rotation, a series of two-dimensional, isocentric projections are recorded by X-ray radiation from different projection directions, the angular region covered by the orbital movement being approximately 200 degrees or more. Subsequently, a spatial representation of the body part under examination is detected from the two-dimensional projections by means of a reconstruction method.

X-ray recording devices equipped with a C-arm also exist that obtain a spatial representation of part of a patient by rotating the X-ray emitter and the X-ray detector around an angulation axis extending in the C-arm plane. Such X-ray recording devices, however, have the drawback that only peripheral areas of the body of the patient and/or the extremities of the patient can be examined.

An X-ray recording device with an X-ray radiation source and an X-ray radiation receiver is known from DE 197 46 092 A1, which are displaceable relative to the object for recording successive two-dimensional projections of an object from different projection directions, and with means for producing a three-dimensional image data set from the recorded two-dimensional projections. The disclosed X-ray recording device has, however, the drawback that slight alterations to the configuration of the arrangement of the object to the X-ray recording device can be made only at increased cost.

A medical device is known from DE 198 27 022 A1, including a device component connected to a holder, the holder having elements that are moveable in a motorized manner relative to one another, and a control and computing unit that controls the motorized relative movements of the elements. This medical device also has means associated with the control and computing unit that allow the determination of straight lines in different spatial directions, along which the device component can be moved in a motorized manner, at least indirectly, by means of the holder. This known medical device, however, has the drawback that it cannot be used as a compact, optionally mobile X-ray recording device. Additionally, with the X-ray recording device disclosed in this publication, the bearing of the stand unit is subject to high mechanical stresses in order to ensure the stability required for such a C-arm holder, consistent with safety standards in medical procedures.

SUMMARY OF THE INVENTION

An object of the invention is to provide an X-ray recording (imaging) device of the aforementioned type in which an alteration to the recording range can be undertaken at reduced cost. Moreover, it is an object of the invention to design the X-ray recording device in a manner which is as space-saving and as stable as possible.

These objects are achieved by an X-ray recording (imaging) device, wherein that the retainer has only one first pivoting arm rotatably mounted on the stand unit, that rotates around a first vertical rotational axis, and only one second pivoting arm rotatably mounted on the first pivoting arm, that rotates around a second vertical rotational axis. Thus the supporting device can be moved within a range of several decimeters without additionally having to move the stand unit. This allows rapid and easy alteration of the position of the X-ray emitter and the X-ray detector, and thus rapid and easy alteration of the recording range. The recording range of the X-ray recording device is precisely the region which is penetrated by the X-ray radiation emitted by the X-ray emitter. The recording range is generally adjustable.

With the X-ray recording device according to the invention, all movements of the supporting device that are known from the prior art can be executed. The retainer, however, in contrast to the prior art, technically of relatively simple and compact configuration. Additionally, with the design of the retainer according to the invention it is possible for the X-ray recording device to be structurally stable without additional support and/or fastening of the X-ray recording device to external fixtures. Thus the safety requirements for the X-ray recording device can also be cost-effectively fulfilled, for example with regard to the stability and nevertheless, for example, a parallel displacement of the supporting device of the X-ray recording device is made possible. As a result, the working conditions of the medical personnel can be cost-effectively improved. Furthermore, the retainer allows spatial representations of an object to be examined to be detected with new projection geometries—namely for tomosynthesis.

The supporting device can be formed by one or more components. For example, the supporting device can be composed of a mechanical connection between the X-ray emitter and the X-ray detector and a guide device attached thereto which, for example, may also embody a drive device. The guide device may be connected, for example, to one end of the second pivoting arm of the retainer in order to be supported thereby on the stand unit.

In an embodiment of the invention, the X-ray recording device has a device center of gravity, the first vertical rotational axis and the second vertical rotational axis extending at a distance from the center of gravity of the device, and the distance in every rotational position of the pivoting arms is so short that the X-ray recording device is configured to be stable at least around a horizontal axis. The X-ray recording device also preferably is not fastened to an external fixture, which is generally regarded as an object that is not associated with the X-ray recording device. Usually, an external fixture is, for example, the floor on which the X-ray recording device is positioned. Frequently, the X-ray recording device is fastened by an anchor in the floor in order to preclude tipping of the X-ray recording device or to enable the X-ray recording device to be put into operation only due to the resulting stable conditions. This is not required with the aforementioned arrangement of the vertical rotational axes. The stability is provided at least for a horizontal axis. Generally, the tipping axes are the connecting axes of the contact components of the X-ray recording device connected to the floor, for example support feet, roller elements or possibly the bottom edge of the stand unit, provided that the stand unit is in contact with the floor with its base. The distance of the vertical rotational axis from the center of gravity of the device is dimensioned such that tipping of the X-ray recording device is precluded within the scope of conventional safety standards. In particular, the distance of the vertical rotational axes from the center of gravity of the device can be selected such that stability is provided for an X-ray recording device, which is possibly not held on an external fixture, around a number of horizontal axes, for example around a second horizontal axis and a third horizontal axis, in order also to prevent tipping to the side, to the front, etc.

The possibility of moving the pivoting arms freely or virtually freely about the vertical axes, and thus always to ensure the stability of the X-ray recording device, increases the examination possibilities of medical personnel examining an object to be examined. The maximum distance which at least one of the vertical rotational axes may be from the center of gravity of the device, is dependent among others on the weight distribution of the X-ray recording device. Generally, by increasing the weight of the stand unit, the maximum distance of the first and the second rotational axes from the center of gravity of the device can also be increased. In one particular case, the first and the second vertical rotational axes always extend, i.e. at every rotational position of the pivoting arms, through the stand unit.

In another embodiment of the invention, the first pivoting arm and/or the second pivoting arm has a displacement device that defines a specific horizontal translation axis. Such a displacement device can be configured, for example, as a telescopic unit integrated in the first and/or the second pivoting arm. As a result, the horizontal distance of the supporting device from the vertical rotational axes of the pivoting arms can be set and adapted to the requirements of the examination. By the use of such a displacement device, it is possible, by superimposing the rotations of the pivoting arms about their vertical axes and a displacement in the direction of the horizontal translation axis determined by the displacement device, to carry out a linear displacement of the supporting device horizontally, perpendicularly to the translation axis determined by the displacement device. In other words, the supporting device can be displaced parallel and/or carry out a parallel displacing translation. By the use of the retainer according to the invention, a displacement and possibly a rotation of the supporting device can be achieved in different horizontal directions, the space requirement being kept as small as possible to allow these movements. The compact design of the retainer and the possibility for carrying out the disclosed movements of the supporting device increase the flexibility, i.e. also the number of applications of the X-ray recording device, in particular the supporting device.

This flexibility of use can be achieved particularly cost-effectively when only one first pivoting arm and only one second pivoting arm—according to the invention—are provided. This is advantageous, in particular, for mobile X-ray recording devices since, due to the necessity of maintaining stability of the X-ray recording device, too large a distance of the supporting device from the stand unit must be avoided as an increased torque is produced, otherwise the X-ray recording device will tip easily, provided that no additional support means are provided. Additionally, it is advantageous that all pivoting arms in the inventive device are arranged horizontally, in order to allow a horizontal 360 degree rotatability of the pivoting arms around each vertical rotational axis, and thus further increasing the flexible use of the X-ray recording device.

In a further embodiment of the invention, a lifting device is provided for raising and lowering the supporting device. The lifting device may be arranged, for example, on the retainer, the stand unit or even on the supporting device. The lifting device allows a manual or motorized vertical movement of the supporting device. The lifting device may be configured, for example, as a toothed rack, which may be moved by a drive device controlled by a control device. As a result, the vertical positional component of the supporting device can be adapted to the boundary conditions of the examination that are present in each case which, for example, can include different heights of patient positioning devices or different designs with regard to the concept of supporting the patient positioning devices.

In a further embodiment of the invention the stand unit is mounted on roller elements. By mounting the stand unit on roller elements, the X-ray recording device may be configured to be mobile. The roller elements therefore, may be configured as cylindrical rollers, cylinders, balls, etc. In particular for mobile X-ray recording devices, a compact retainer that does not negatively influence the stability is important. The possibility of displacing the supporting device with mobile X-ray recording devices in specific spatial regions horizontally and/or vertically, without having to move the stand unit mounted on rollers, brings considerable advantages to the examination of stationary objects to be examined, namely bedridden patients—in everyday clinical use.

In a further embodiment of the invention, a compensation arrangement is provided for compensating for displacement of the center of gravity of the device due to a movement of the supporting device. Such an arrangement, for example, may be configured as radial arms or support. If the supporting device is moved by the retainer according to the invention, generally it leads to a displacement of the center of gravity of the X-ray recording device. The displacement of the center of gravity of the device may lead to a reduction of the stability of the X-ray recording device and thus also to tipping, in particular lateral tipping, of the entire X-ray recording device. In order to allow sufficient freedom of movement of the supporting device, in particular a sufficient range for the parallel displacement, and at the same time to avoid the occurrence of variable stability of the X-ray recording device, which may arise by an alteration of the location and/or position of the supporting device, the compensation arrangement compensates for the displacement of the center of gravity. For example, large-mass motor-driven radial arms controlled by a control device may be provided which, depending on the location and/or position of the supporting device, alter the weight distribution of the X-ray recording device such that the center of gravity of the device remains unaltered. The compensation of the alteration of the position of the center of gravity of the device takes place preferably at the same time as the movement of the supporting device, so that the stability and/or solidity of the X-ray recording device is provided for every location and/or possibly position of the supporting device.

In another embodiment of the invention, a sensor is provided for detecting a location and/or position of the supporting device. The location, detected by the at least one sensor, and/or the position of the supporting device, is/are supplied to the control device which, on the basis of the supplied location and/or position of the supporting device, controls the compensating means such that the position of the center of gravity of the device remains substantially unaltered. Thus, during the movement of the supporting device it is already possible for the X-ray recording device to be stable. The sensor and/or a sensor system may, for example, be configured as an optical or electromagnetically configured position detection system.

In a further embodiment of the invention the supporting device has a C-arm defining a C-arm plane. The X-ray emitter and the X-ray detector, therefore, are generally arranged opposite one another, aligned with one another on the C-arm. The C-arm X-ray device may be suitable for detecting spatial representations of an object to be examined—three-dimensionally-capable C-arm X-ray device—or also may be configured as a technically more simple two-dimensionally-capable C-arm X-ray device. C-arm X-ray devices are a frequently used medical device, in particular in everyday clinical use. By enabling parallel displacements and isocentric rotations of the C-arm by means of the retaining means according to the invention, which are configured to be compact and technically simple, the maneuvering of the C-arm to the examination area provided, of the object to be examined, is considerably facilitated, in particular when the size of the examination area exceeds the amount of X-ray radiation—of the recording range—penetrating the object to be examined.

In a preferred embodiment of the invention, the control device is configured such that the C-arm can be rotated about a rotational axis that is perpendicular to the C-arm plane. Thus the C-arm can be rotated along its circumference around an orbital axis, which allows a detection of a plurality of two-dimensional projections of the object to be examined, from which a spatial representation of the examination area can be detected. The rotation around the orbital axis is generally controlled by the control device and effected by an orbital drive.

In a further embodiment of the invention, a control device is configured such that the C-arm can be rotated around the first vertical rotational axis and/or about the second vertical rotational axis. By means of the control device, for example, the movements of the C-arm can be restricted to a specific spatial area, in order to prevent instability of the X-ray recording device by disadvantageous static weight distributions. The movement of the C-arm around one or both vertical rotational axes can be effected manually or by motor. The C-arm, possibly without restricting the spatial area, can be rotated by 360 degrees around one or both vertical rotational axes, provided that the stability of the X-ray recording device is always maintained. One advantage of a C-arm that can be adjusted only by motor is that inadvertent movements and/or adjustments of the position of the C-arm about the vertical rotational axes—namely by an inadvertent impact—can be eliminated.

In a further preferred embodiment of the invention a control device is configured such that the C-arm can be rotated around a horizontal rotational axis extending in the C-arm plane. As a result, the C-arm can be executed at least one angulation movement around the object to be examined, in order to detect projection data sets of the object to be examined. The angular rotation may be carried out both manually and by motor and may be used for the detection of spatial representations of the object to be examined.

In a further preferred embodiment of the invention, a control device is configured such that the C-arm can be rotated around a vertical rotational axis extending in the C-arm plane. Such a rotation, for example an isocentric rotation around a vertical axis extending through the C-arm plane, is possible with the retainer according to the invention and further increases the flexibility of use of the X-ray recording device according to the invention. It is advantageous, in particular, that such a movement can be carried out by compact and technically simple structure/components. The rotation around the vertical rotational axis may be carried out by motor or manually and also allows examinations of patients in the seated position.

The control device is preferably designed as a central unit of the X-ray recording device which is configured for all movements to be performed by the supporting device. The configuration is carried out, for example, by means of programmable routines, which are stored in the control device and may be executed by the control device. The drive devices cooperating with the control device which, for example, effect the rotation of the supporting device about vertical and horizontal axes, the displacement of the displacement device and/or the lifting device, etc. are generally arranged at different positions on the X-ray recording device and are conceived and designed for the respective function.

In a preferred embodiment of the invention, a collision avoidance arrangement is provided for avoiding collision of the supporting device with an object. An object may, for example, be a component of the X-ray recording device, a component of a medical work station, spatial limitations or even the object to be examined. This arrangement, for example, can be configured as sensors for detecting the approach of an X-ray device component to an object, and which cooperate with the control device. If a minimum distance is exceeded, the examination is interrupted. A further possibility for avoiding a collision is to carry out a simulation of the examination. In this version, for example, the boundary conditions of the examination are supplied to the control device. An examination path of the supporting device carried out virtually shows whether a collision would occur when the examination is carried out in real time. Based on the simulation, the boundary conditions and/or the examination parameters, for example the examination path to be covered by the X-ray emitter and the X-ray detector, can be altered such that a collision is avoided.

DESCRIPTION OF THE PREFERRED EMBODIMENTS

Figure 1:
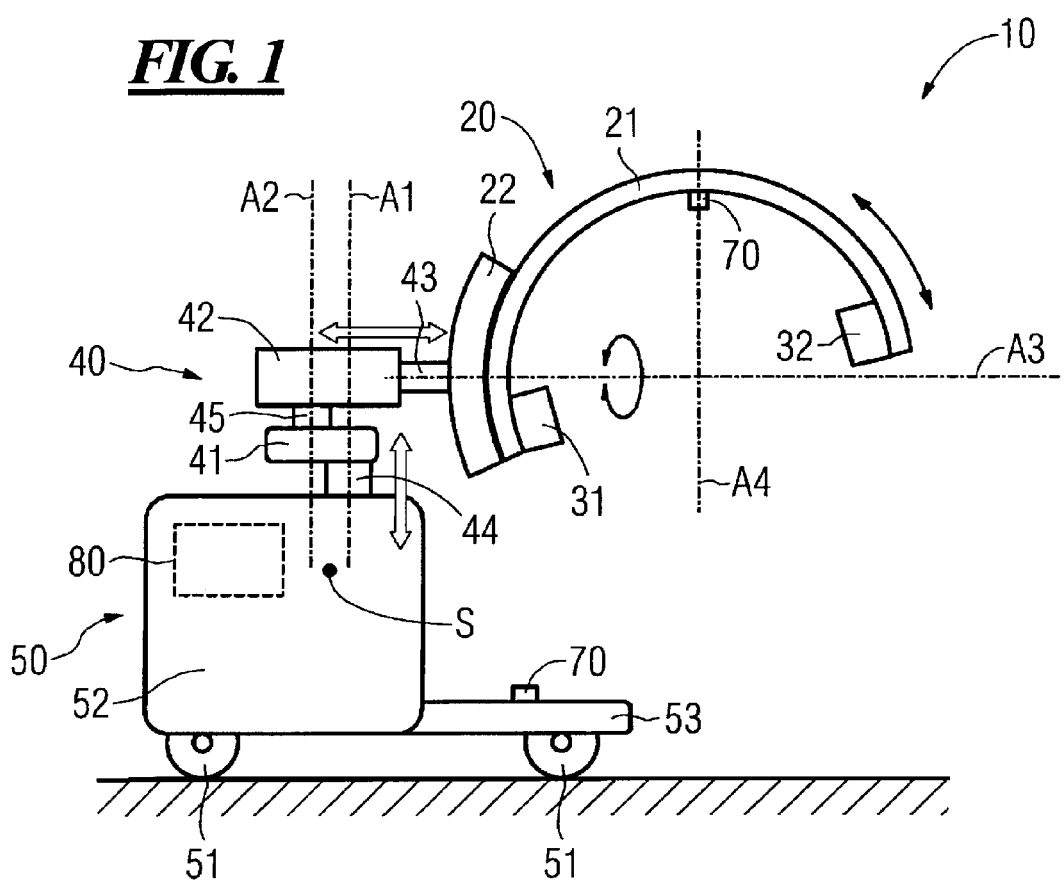
FIG. 1 is a schematic side view of a mobile C-arm X-ray device according to the invention.

FIG. 1 shows a mobile C-arm X-ray device 10 with a supporting device 20, which is supported by a retainer 40 on a stand unit 50. The supporting device 20 has a C-arm 21 spanning a C-arm plane and a drive device 22 which is simultaneously configured as guide means and fastening means for the C-arm 21. A rotation of the C-arm 21 is effected by the drive device 22 along its circumference—an orbital rotation—around an orbital axis A5 shown in FIG. 2, as well as a rotation around a horizontal angulation axis A3. Additionally, the retaining means 40 allow a rotation of the supporting device 20 about a vertical axis A4 extending in the C-arm plane. To detect two-dimensional projections of an object to be examined, not shown in FIG. 1, an X-ray emitter 31 and an X-ray detector 32 are provided which are arranged opposite one another, aligned on the C-arm 21. The relative location and position of the X-ray detector 22 and the X-ray emitter 21 always remain unaltered relative to the C-arm 21.

The stand unit 50 has roller elements 51 allowing the X-ray recording device 10 to freely move and, therefore, to be suitable for examinations of stationary objects to be examined. The X-ray recording device 10 shown in FIG. 1 has three rollers S1 arranged in the form of a triangle on the underside of the stand. To increase the stability of the mobile X-ray recording device 10 the stand unit 50 has, in the vicinity of the floor, an extension—namely a stand toe 53 that extends to below the C-arm 21 and on which a roller element 51 is arranged. The two further roller elements 51 are located below the stand tower 52 enclosed by the stand unit 50. The stand unit 50 additionally comprises a control device 80 in which the methods for operating the X-ray recording device 10 are stored and cooperates with the drive device 22. The stand unit 50 is mechanically connected via the retaining means 40 to the supporting device 20. The retainer 40 has a first pivoting arm 41 and a second pivoting arm 42 which can be rotated about a first vertical rotational axis A1 and a second vertical rotational axis A2. The retainer 40 further includes a lifting device 44 and/or vertical displacement device, with which the height of the pivoting arms 41 and/or 42 can be adjusted and thus also the height of the supporting device 20. Moreover, a horizontal displacement device 43 is provided with which the distance of the supporting device 20 from the second vertical axis A2 along the second pivoting arm 42 can be set. Alternatively the horizontal displacement device 43 can be arranged on the stand unit 50, for example in the form a rail guide for the lifting device 44, whereby a mobile element can be dispensed with on the pivoting arm 42. The vertical spacing of the first pivoting arm 41 from the second pivoting arm 42 is achieved by a bearing device 45, which possibly allows the vertical distance from the first pivoting arm 41 to the second pivoting arm 42 to be set. Furthermore, a sensor 70 is provided on the stand unit 50 and a sensor 70 on the supporting device 20, preferably on the C-arm 21. These sensors 70 serve to detect the location and/or possibly the position of the supporting device 20 and/or of the C-arm 21 relative to the stand unit 50.

The X-ray recording device 10 has a center of gravity of the device S resulting from the weight distribution of the X-ray recording device components—namely the stand unit 50, the supporting device 20 and the retainer 40.

Figure 2A:
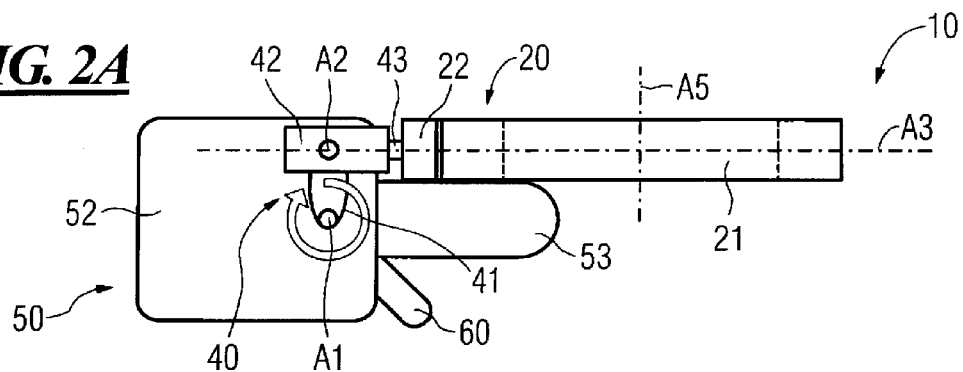
FIGS. 2A, 2B and 2C respectively are schematic plan views of the mobile C-arm X-ray device with various positions of a parallel-displaced supporting device, according to the invention.
Figure 2B:
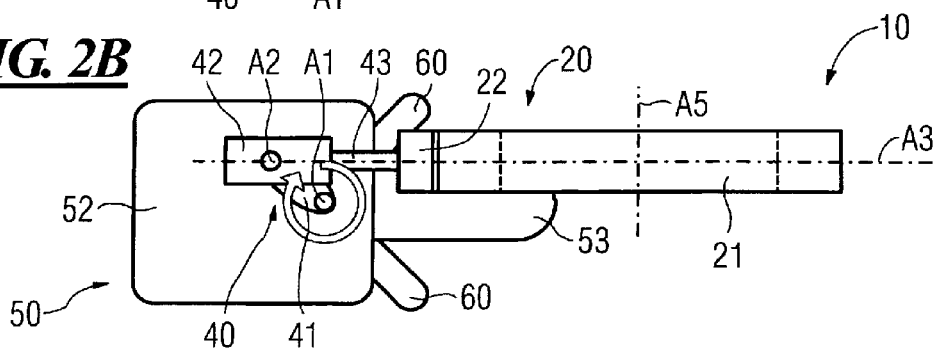
Figure 2C:
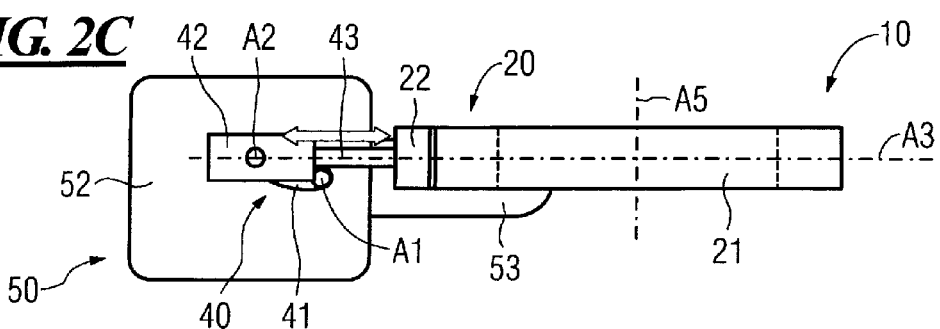

FIGS. 2A, 2B and 2C show plan views of the X-ray recording device 10 of FIG. 1 with different positions of the supporting device 20 relative to the stand unit 50, the supporting device 20 being displaced parallel along the front face of the stand unit 50. At the left of FIGS. 2A, 2B and 2C, the supporting device 20 is shown in an edge position and/or marginal position. The first pivoting arm 41 and the second pivoting arm 42 are located at an angle of 90 degrees to one another, so that the horizontal angulation axis A3 extends parallel to the translation axis determined by the displacement device 43. The plane spanning through the C-arm 21 extends substantially parallel to, and in the vicinity of, the left-hand boundary of the stand unit 50. The distance of the second vertical rotational axis A2 from the supporting device 20 is, therefore, set by the displacement device 43 such that the supporting device 20 is arranged in the vicinity of the stand unit 50, without being in contact therewith.

If the supporting device 20 is located in an edge position, the susceptibility to lateral tipping and/or the stability of the X-ray recording device 10 is increased as the center of gravity of the device S of the X-ray recording device 10 has been displaced away from its original position. To prevent the displacement of the center of gravity of the device S from its substantially central position, which provides the stability of the X-ray recording device 10, an arrangement is provided for compensating for the weight displacement produced by the edge position of the supporting device 20 and thus the displacement of the center of gravity of the device. The weight displacement compensation arrangement 60 can be entirely inside the stand unit 50, entirely outside, or according to the amount of weight displacement to be compensated, partially inside, partially outside the stand unit 50, as implemented in the embodiment. The weight displacement compensation arrangement 60 has a large-mass arranged such that the arrangement 60 is able to alter its location and/or possibly position depending on the location and/or position of the supporting device 20, such that the position of the center of gravity of the device S of the X-ray recording device 10 remains substantially unaltered for different locations and/or positions of the supporting device 20. In FIGS. 2A and 2B the weight displacement compensation arrangement 60 is configured as extendable left-hand and right-hand radial arms which may be extended independently of one another.

If the supporting device 20 is located in the vicinity of a central position in front of the stand unit 50, the X-ray recording device 10 is generally stable. The radial arms of the arrangement 60 are retracted in this position of the supporting device 20 and arranged in the vicinity of the center of gravity of the device S. If the supporting device 20 is moved into a marginal position, the weight is displaced which is caused by the altered position of the supporting device 20 and which produces a torque about the respective wheel base axis, i.e. the connecting axis between one of the two roller elements 51 arranged below the stand tower 52 and the roller element 51 which is arranged on the stand toe 53. The origin of the torque can be seen in the displacement of the center of gravity of the device 5, which is effected by the alteration of the location and/or position of the supporting device 20. In order to counteract the occurrence of this torque, radial arms of the arrangement 60 located respectively on the opposing side to the position of the supporting device 20 are extended, in order to counteract an change of the position of the center of gravity of the device S. Preferably the extension of the radial arms 60 is carried out simultaneously with the alteration of the position of the supporting device 20. Thus at any point, a stable position of the X-ray recording device 10 is provided as the position of the center of gravity of the device S always remains substantially unaltered.

In order to allow a parallel displacement of the supporting device 20 the first pivoting arm 41 is rotated about the first vertical rotational axis A1. The position of the second pivoting arm 42 remains unaltered relative to the supporting device 20 and thus alters its position relative to the first pivoting arm 42. With the parallel displacement, the distance between the supporting device 20 and stand unit 50 is to be kept constant. This is made possible by the displacement device 43. The displacement device 43 compensates for the movement component parallel to the angulation axis A3, produced by the rotation of the first pivoting arm 41 about the first vertical rotational axis A1, by an extension or shortening, for example, of the displaceable arm. Thus a parallel displacement of the supporting device 20 may be possible with any rotational direction about the first vertical rotational axis A1, whereby an examination of an extended examination area of an object to be examined is facilitated along axis A5.

Figure 3:
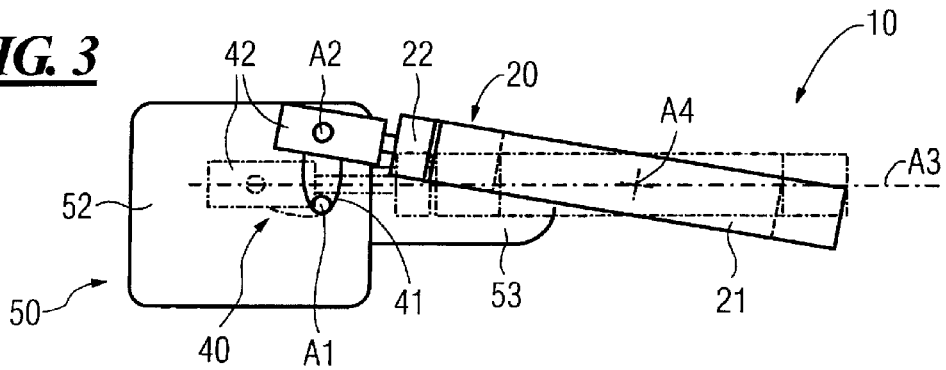
FIG. 3 is a schematic plan view of a mobile C-arm X-ray device with an isocentrically rotated supporting device according to the invention.

FIG. 3 shows the X-ray recording device 10 of FIG. 1 in a plan view of two different positions of the supporting device 20. In the first position, the supporting device 20 is located centrally in front of the stand unit 50. In the second position the supporting device 20 is located in a marginal position made possible by the retaining means 40, for adopting the marginal position, an isocentric rotation of the supporting device 20 and/or the C-arm 21 about a vertical rotational axis A4 extending in the C-arm plane having been additionally carried out. The C-arm 21 is thus preferably symmetrically arranged about the vertical rotational axis A4, i.e. the intersection of the rotational axis A4 with the C-arm 21 is located in the center of the C-arm. The angular range covered by means of the isocentric rotation is, among others, dependent on the length of the pivoting arms 41 and/or 42. An isocentric rotation of the supporting device 20 is preferably controlled by the control device 50. In this regard, the supporting device 20 can be transferred from the left-side marginal position into the right-side marginal position and thus carry out an isocentric rotation. The fixing of the isocenter is carried out as in FIG. 2 via the displacement device 43. It should be noted that the translation axis defined by the displacement device 43, along which the supporting device 20 may now be horizontally displaced, is no longer able to be located parallel to the angulation axis A3.

Although modifications and changes may be suggested by those skilled in the art, it is the intention of the inventor to embody within the patent warranted hereon all changes and modifications as reasonably and properly come within the scope of the inventor's contribution to the art.

We claim:

1. An x-ray recording device comprising:
   an x-ray emitter that emits x-rays;
   an x-ray detector that detects said x-rays after passage through an examination subject;
   a supporting device on which said x-ray detector and said x-ray emitter are mounted so that said x-rays, after penetrating said subject, strike said detector;
   a stand unit;
   a retainer mechanically connected between said stand unit and said supporting device, said retainer comprising only one first pivoting arm, rotatably mounted on said stand unit for rotation around a first vertical rotational axis, and only one second pivoting arm, rotatably mounted on said first pivoting arm for rotation around a second vertical rotational axis;
   a displacement arm mechanically connected between said stand unit and said supporting device that is extendable and retractable to displace said supporting device toward and away from said stand unit along a horizontal displacement axis that is perpendicular to a horizontally extending longitudinal axis;
   a drive arrangement in driving connection with each of said first and second pivoting arms and said displacement device; and
   a control unit that operates said drive arrangement to move said support arm along said longitudinal axis, by rotating said first and second pivoting arms relative to each other and relative to said stand unit to cause said supporting device to execute movements relative to said stand unit that tend to move the supporting device out of perpendicularity with said longitudinal axis, and by expending and retracting said displacement arm in coordination with rotation of said first and second pivoting arms to compensate for said movement out of perpendicularity with said longitudinal axis, to always maintain said support device perpendicular to said longitudinal axis while moving said support device along said longitudinal axis.

2. An x-ray recording device as claimed in claim 1 wherein said x-ray detector, said x-ray emitter, said supporting device, said retainer, and said stand unit form an unanchored component combination exhibiting a center of gravity, and wherein said first vertical rotational axis and said second vertical rotational axis extend at respective distances from said center of gravity, and wherein said retainer is configured to cause said respective distances, for every rotational position of said first pivoting arm and said second pivoting arm, to be sufficiently short to preclude tipping of said unanchored component combination.

3. An x-ray recording device as claimed in claim 2 wherein said stand unit is a mobile, wheeled cart.

4. An x-ray recording device as claimed in claim 1 comprising a lifting device that raises and lowers said supporting device relative to said retainer and said stand unit.

5. An x-ray recording device as claimed in claim 1 wherein said stand unit comprises roller elements at a bottom thereof.

6. An x-ray recording device as claimed in claim 1 comprising a sensor that detects at least one of a spatial location and a spatial position of said supporting device relative to said stand unit.

7. An x-ray recording device as claimed in claim 1 wherein said supporting device is a C-arm defining a C-arm plane.

8. An x-ray recording device as claimed in claim 7 wherein said control device is configured to operate said drive arrangement to rotate said C-arm around a rotational axis oriented perpendicularly to said C-arm plane.

9. An x-ray recording device as claimed in claim 7 wherein said control device is configured to operate said drive arrangement to rotate said C-arm around at least one of said first vertical rotational axis and said second vertical rotational axis.

10. An x-ray recording device as claimed in claim 7 wherein said control device is configured to operate said drive arrangement to rotate said C-arm around a horizontal rotational axis in said C-arm plane.

11. An x-ray recording device as claimed in claim 7 wherein said control device is configured to operate said drive arrangement to rotate said C-arm around a vertical rotational axis in said C-arm plane.

12. An x-ray recording device as claimed in claim 1 comprising a collision-avoidance arrangement associated with said supporting device that prevents said supporting device from colliding with an object.

13. An x-ray recording device as claimed in claim 1 wherein said x-ray detector, said x-ray emitter, said supporting device, said retainer and said stand unit form an unanchored combination exhibiting a center of gravity, and wherein movement of said supporting device on said retainer displaces said center of gravity, and comprising a weight compensation arrangement that compensates for torque produced by said center of gravity to preclude tipping of said unanchored component combination.

14. An x-ray recording device as claimed in claim 13 wherein said stand unit is a mobile, wheeled cart.

* * * * *